United States Patent [19]

Wallström

[11] Patent Number: 4,762,520
[45] Date of Patent: Aug. 9, 1988

[54] ABSORBENT ARTICLE

[75] Inventor: Leif Wallström, Mölnlycke, Sweden

[73] Assignee: Molnlycke AB, Gothenburg, Sweden

[21] Appl. No.: 13,987

[22] PCT Filed: Jun. 10, 1986

[86] PCT No.: PCT/SE86/00278

§ 371 Date: Jan. 16, 1987

§ 102(e) Date: Jan. 16, 1987

[87] PCT Pub. No.: WO86/07242

PCT Pub. Date: Dec. 18, 1986

[30] Foreign Application Priority Data

Jun. 11, 1985 [SE] Sweden .................. 8502889

[51] Int. Cl.⁴ ............................................. A61F 13/16
[52] U.S. Cl. ..................................... 604/366; 604/370
[58] Field of Search ............... 604/366, 367, 370, 371, 604/358, 385.1

[56] References Cited

U.S. PATENT DOCUMENTS 3,056,406 10/1962 Ness ................................... 604/370

FOREIGN PATENT DOCUMENTS 1610523 7/1971 Fed. Rep. of Germany .
432515 4/1984 Sweden .
748191 4/1956 United Kingdom .
774793 5/1957 United Kingdom .

*Primary Examiner*—John D. Yasko
*Attorney, Agent, or Firm*—Young & Thompson

[57] ABSTRACT

An absorbent article such as a sanitary napkin or a diaper comprises an absorption body (9) accommodated in a casing (11). The casing is composed of a carded fiber fabric made in one piece and containing at least 5% of melt fibers, preferably polypropylene, sub-divided into parallel streaks (1, 3, 4, 5, 6) having different melt-bonded patterns. There are thus provided streaks of varying structures which are adapted to their individual positioning in relation to the absorption body (9). The casing (11) seals around the absorption body (9) with at least two layers (6, 2) on the side of the absorption body facing the user, the outermost layer (2) having a substantially tighter bonding pattern than the inner, loosely bonded and voluminous layer(s).

4 Claims, 2 Drawing Sheets

ABSORBENT ARTICLE

The present invention relates to an absorbent article such as a sanitary napkin or a diaper, comprising an absorption body accomodated in a casing.

For the absorption of human body fluids by means of disposable absorbent articles, it is extremely important that the construction of the product in question allows for the body-contacting layer to remain dry, i.e. so as to prevent rewetting of the user's skin. For this purpose it is common practice in today's manufacture of absorbent articles to have the casing made of hydrophobic material. A casing of this type normally consists of fiber fabric which for practical reasons, e.g. for providing a sufficient degree of wear resistance, is firmly and tightly bonded. As a result, however, the fiber fabric will be comparatively thin and incapable of preventing in a satisfactory manner rewetting with fluid from the absorption body. No insulating effect is thus obtained with this thin fiber layer since fluid from the absorption body will easily penetrate it thereby making a product provided with this type of casing unpleasant to wear.

Previous attempts have been made to overcome this problem by applying specific insulating layers between the surface layer and the absorption core. For this purpose an airlaid layer of hydrophobic fibers, or fibers coated with a hydrophobic agent, has shown to function well as an insulating layer, but has also proved inappropriate with regard to manufacture because of the difficulties associated with the application of such layers at a high manufacturing speed while simultaneously fulfilling the demands on quality. Insulating layers in web shape have also been utilized. In this context there is however the problem that such factors as strength and insulating capacity are difficult to combine in the web material. If a voluminous insulating layer is desired, the resistance to tensile stress arising in the web material during manufacture will necessarily be poor.

The present invention has for its object to accomplish an improved casing for absorbent articles with a well-functioning insulating layer by means of which the problems touched upon above would be totally eliminated. For this purpose, an absorbent article made in accordance with the invention and being of the type set forth in the introduction is primarily distinguished by the casing consisting of a carded fiber fabric made in one piece and containing at least 5% of melt fibers, preferably of polypropylene, said casing being subdivided into parallel streaks having different melt-bonded patterns, producing in this manner varying structures in the streaks adapted to their individual positioning in relation to the absorption body.

In a suitable embodiment of the article in question, the casing seals around the absorption body with at least two layers on the side of the absorption body facing the user.

To advantage, the outermost of these layers has a substantially tighter bonding pattern than the loosely bonded and voluminous interior layer(s).

As a consequence of the casing for the inventive absorbent article being composed of a plurality of coherent parallel streaks, one ore more streaks serving as insulating layers can be given a highly voluminous shape, since the tensile stress in the longitudinal direction of the manufacturing web could be taken up by the other streaks included in the casing material.

The invention will be more closely described in the following with reference to the accompanying drawing, of which FIG. 1 is a plan view of a first exemplary embodiment of a casing for an absorbent article made according to the invention;

Figure 1:
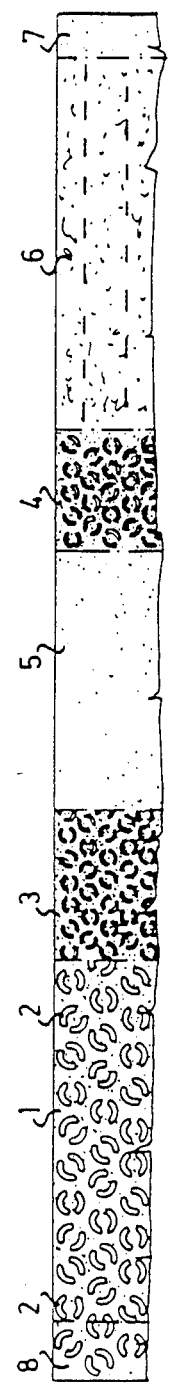

FIG. 1 illustrates a section of a carded fiber fabric web intended to serve as a casing for an absorbent article according to the invention. The fiber fabric web, formed as a continuous length and containing melt fibers, is subdivided into various parallel streaks each one structured to have the specific property suiting its contemplated position around the absorption body. The unbroken web of material contains at least 5% of polypropylene fibers and may also include elements of rayon and/or bicomponent fibers. The streak 1 which is located to the left in FIG. 1 and which, when applied to the absorbent article, constitutes the surface material lying in direct contact with the user's skin, should be soft and pleasant but still resistant to wear. According to the exemplary embodiment, this function has been accomplished by means of melt-bonding to the binding pattern shown in FIG. 1. This pattern, desgined in the form of non-closed rings 2, has proved most advantageous due to its softness, pliability and wear resistance. Two of the streaks, 3 and 4, have identical patterns and are intended to constitute the edge portions of the casing for an absorbent article, which will be described in the following.

These two streaks 3 and 4 have a bonding pattern which, in comparison with that of the previously mentioned streak 1, consists of smaller and more tightly applied non-closed circles 2. In this manner, a higher strength is imparted to the streaks 3 and 4 in comparison with the first-mentioned streak 1. Arranged between the two streaks 3 and 4 is a smooth-calendered streak 5 intended to constitute the back of the absorbent article. The reason for the streak 5 being smooth-calendered is the contemplated use of the fiber fabric web illustrated in the embodiment as a casing for a sanitary napkin, for which purpose the back of the casing should be coated with a binding agent adhering to the user's underwear. In fact, the consumption of glue for achieving a certain adhesive effect will be minimized if the binder is applied to a smooth material. The streak 6, intended to serve as the liquid insulating layer of the casing, is very loosely bonded and thus voluminous. Owing to the poor strength of the loosely bonded streak 6, there is located to the right in FIG. 1 an edge streak 7 which is smooth-calendered and acts as a reinforcement for taking up tensile stresses in the web material in its entirety. The opposed edge portion of the web, designated by 8 in the figure, has the same type of bonding as the adjoining streak 1.

Figure 2:
FIG. 2 shows a cross section through the casing of FIG. 1.

FIG. 2 illustrates in cross section the fiber web as seen in FIG. 1. According to the embodiment shown, this web is made of fibers uniformly spaced over the whole width of the web. The bonding pattern and the compression during calendering of the fiber fabric web will give each individual streak varying properties. As is clearly apparent from FIG. 2, the loosely bonded streak designated by 6 is considerably thicker than the other streaks and will therefore provide good insulation.

Figure 3:
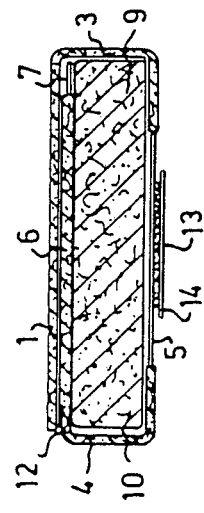
FIG. 3 shows a cross section through an absorbent article provided with a casing according to FIGS. 1 and 2.

FIG. 3 illustrates in cross section an example of an absorbent article designed as a sanitary napkin. This article has an absorption core 9 of fluff pulp, for example, and a liquid impermeable plastic film 10 extending across one side surface of the absorption core; the bottom side, with portions 11 covering both side edges of the absorption core. A casing 11 of the kind shown in FIG. 1 and 2 is applied around the absorption core 9 and the liquid permeable film 10. This construction of the sanitary napkin will enable the use of an extremely simple manufacturing method, because the plastic film 10 and the casing 11 may then be positioned around the absorption core in one and the same folding operation. The casing obtained in this manner is sealed by one of its edge streaks 8 being glued onto the streak 4 extending along one upper edge 12 of the sanitary napkin. The streak 2 intended for direct contact with the user's skin is then situated right on top of the voluminous insulating streak 6, which during use of the article will effectively prevent the user's skin from being rewetted with moisture from the absorption core 9. By securing the casing at 12 in FIG. 3 along one edge of the sanitary napkin face, no binder beads will inhibit the desirable flow of fluid through the outer layer, while simultaneously the entire area of the napkin upper face will be covered by the streak designated by 1 and having the properties adapted for this purpose.

On the back of the sanitary napkin, binder 13 is applied at the center of the smooth-calendered streak 5 of the casing. The biner coating 13 is covered with a release paper 14. Finally the casing is conventionally cross-sealed at either end of the absortpion core.

Figure 4:
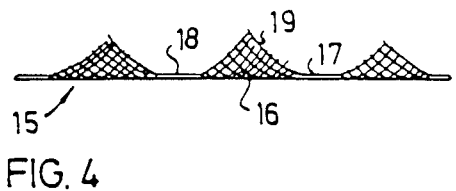
FIG. 4 shows to a larger scale a cross section through a streak in a casing according to a second exemplary embodiment.

FIG. 4 illustrates in cross section and to a larger scale a streak of fiber fabric intended as a casing for an absorbent article according to a second embodiment of the invention. Within this streak, one side 16 of the fiber fabric 15 is smooth-calendered, whereas the opposite side 17 is pattern-calendered at attachment points 18. Because one side of the fiber streak is smooth-calendered, at least one of each fiber end will be securely affixed. By the outgoing fiber ends 19 on the other side there is obtained a certain volume in the fiber streak, which makes it useful as an insulating layer for absorbent articles such as sanitary napkins and diapers.

Figure 5:
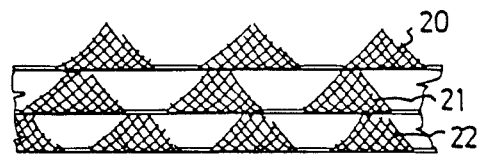
FIG. 5 shows a similarly enlarged cross section through a liquid insulating layer built up of streaks of the type shown in FIG. 4; whereas finally

FIG. 5 illustrates an insulating layer consisting of three superimposed layers 20, 21, 22 of the kind shown in FIG. 4. These three layers are all oriented in one and the same direction, whereby free fiber ends of an underlying layer 21, 22 will be brought into contact with the smooth-calendered side of an adjoining upper layer 20 or 21, respectively. All three layers 20, 21 and 22 produce a non-return valve effect in the sense that fluid is allowed to flow through an upper layer 20 or 21 and down to an underlying layer 21 or 22, respectively, but not in the reverse direction. Upon discharge of body fluids from the user of an absorbent article provided with such an insulating layer, the liquid pressure and force of gravity act to spread this fluid down through all three layers. There is no risk, however, of rewetting occurring in the direction from the absorption core and to the user. Fluid may be spread in the compact, planar bottom layer but not up towards the free fiber ends, which is due to the fact that fluid cannot spread from a tightly compressed, fine-capillary fiber layer to a substantially uncompressed, coarse-capillary fiber layer and against the force of gravity.

Figure 6:
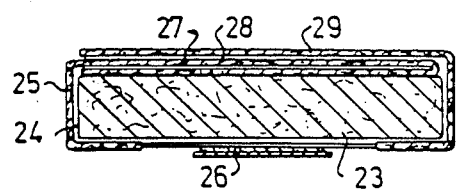
FIG. 6 shows an absorbent article made according to the invention and provided with the liquid insulating layer as seen in FIG. 5.

FIG. 6 illustrates a sanitary napkin which, in accordacne with the invention, is accommodated in a casing containing an insulating layer of the kind disclosed in FIG. 5. This napkin comprises an absorption body 23, a liquid impermeable layer 24 and an integrally formed casing 25 applied to which is a binder coating 26 covered with a release paper. According to the invention, the casing is made with different web streaks each one being performed with regard to its respective function and positioning around the absorption body. Three of these web streaks 27, 28 and 29 are formed to constitute in combination an insulating layer of the kind set forth in FIG. 5. When applying the casing 25 around the absorption core 23, the web streak designated by 27 is first folded in over the web streak designated by 28, and the casing is then applied as previously described with reference to FIG. 3.

The invention is not restricted to the embodiments described above, but a plurality of modifications are conceivable within the scope of the patent claims.

For example, the design of the casing and the absorption body can be varied in many ways. The essential factor is to have the casing made integral with different parallel web streaks formed with due regard to their individual function and positioning around the absorption body.

To advantage, the casing is produced in line with the manufacture of the remaining part of the absorbent article, as it would then be possible to have the casing dimensioned for direct adaptation to the product, avoiding in this manner unneccessary waste of material. The fiber fabric used is formed by carding, whereafter the individual web streaks are produced by diversified calendering, which can be done either by using one single roller with various calendering patterns provided along its length, or by means of several different calender rollers.

I claim:

1. An absorbent article such as a sanitary napkin or a diaper, comprising an absorption body (9) accommodated in a casing (11), characterized by the casing being composed of a carded fiber fabric made in one piece and containing at least 5% of melt fibers, preferably of polypropylene, and by being sub-divided into parallel streaks (1, 3, 4, 5, 6) having different melt-bonded patterns, resulting in streaks of varying structures adapted to their individual positioning in relation to the absorption body (9), the casing (11) sealing around the absorption body (9) with at least two layers (6, 2) on the side of the absorption body facing the user, the outermost layer (2) having a substantially tighter bonding pattern than the inner, loosely bonded and voluminous inner layer(s) (FIG. 3).

2. An absorbent article according to claim 1, characterized in that the layers of the casing (11) are smooth-calendered on their side (16) facing the absorption body (23) and pattern-calendered on their opposite side, producing thereby a non-return valve effect which enables fluid to flow through said layers only in the direction towards the absorption body (FIGS. 4–6).

3. An absorbent article according to claim 1, characterized in that the casing (11) is sealed around the absorption body by means of a binder bead extending along an edge portion (12) on the side facing the wearer during use, and in that the casing is sealed beyond either end of the absorption body (9).

4. An absorbent artile according to claim 1 characterized in that the streak (5) of the casing positioned on the side facing away from the wearer during use is smooth-calendered so as to provide a surface which is suitable for the application of a coating (3) serving as an attachment means adhering to the user's underwear.

* * * * *